United States Patent [19]

Hanessian et al.

[11] Patent Number: 4,663,451

[45] Date of Patent: May 5, 1987

[54] PROCESS FOR THE SYNTHESIS OF PENEMS AND PENAMS

[75] Inventors: Stephen Hanessian, Beaconsfield, Canada; Angelo Bedeschi, Milan, Italy

[73] Assignee: Farmitalia Carlo Erba S.p.A., Milan, Italy

[21] Appl. No.: 645,289

[22] Filed: Aug. 29, 1984

[51] Int. Cl.⁴ .................. C07D 499/00; A61K 31/425
[52] U.S. Cl. .................................... 540/304; 540/313; 514/192; 540/360
[58] Field of Search ................. 260/245.2 R; 540/313, 540/306; 514/192

[56] References Cited

U.S. PATENT DOCUMENTS 4,395,418  7/1983  Ohki et al. .................. 260/245.2 R
4,500,457  2/1985  Girttli et al. ................ 260/245.2 R

*Primary Examiner*—Nicholas S. Rizzo
*Attorney, Agent, or Firm*—Oblon, Fisher, Spivak, McClelland & Maier

[57] ABSTRACT

Described is a novel process for the preparation of penams and penems useful as antibacterial agents, which comprises the reaction of an appropriate 4-substituted-azetidin-2-one with a base, followed by reaction of the thereby formed penam compound with an oxidating agent and a organic or inorganic base.

Also described are novel penam compounds useful as antibacterials which are prepared by the described process.

9 Claims, No Drawings

PROCESS FOR THE SYNTHESIS OF PENEMS AND PENAMS

This invention relates to a novel process useful in the synthesis of penems and penams having antibacterial activity and to novel compounds produced thereby.

More particularly, this invention relates to a process for preparing compounds of the following formula (I):

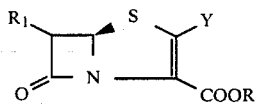

in which R represents a hydrogen atom, a lower alkyl,2,2,2-trichloroethyl, acetonyl, allyl, benzyl, p-nitrobenzyl, p-methoxybenzyl, phenyl, o-nitrophenyl, benzhydryl or 1-phenoxyethyl group or a residue known to be hydrolysed "in vivo" and having favourable pharmacokinetic properties such as an acetoxymethyl, pivaloyloxymethyl or phthalidyl group or a group of the formula $$-\underset{CH_3}{\underset{|}{CH}}-OCOOC_2H_5 \text{ or } -CH_2NHCOR_2$$

in which $R_2$ represents an alkyl group having from 1 to 5 carbon atoms or an aryl group; $R_1$ represents a hydrogen atom, a lower alkyl, lower alkoxy, $C_4$-$C_6$ cycloalkyl, or hydroxyalkyl group, preferably a hydroxy substituted lower alkyl group such as 1-hydroxyethyl, the alcoholic function of the hydroxyalkyl group being free or protected, the protecting group (PG) preferably being a p-nitrobenzyloxycarbonyl, dimethyl-t-butylsilyl, diphenyl-t-butylsilyl, 2,2,2-trichloroethoxycarbonyl, trimethylsilyl, benzyl, p-bromophenacyl, triphenylmethyl or pyranyl group, and Y represents:

(a) a hydroxymethyl group,
(b)

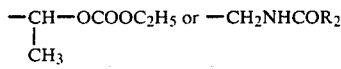

wherein $R_3$ is hydrogen atom, lower alkyl, aralkyl, aryl, heteroalkyl, alkenyl or alkynyl of 2–6 carbon atons, cycloalkyl of 4–6 carbon atoms, optionally substituted by hydroxy, thiol, alkylthio, lower alkyl, lower alkoxy, halogen, cyano, carboxy, nitro, amino, amino lower alkyl or halo lower alkyl and Z is oxygen or sulphur atom;

(c)

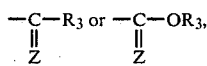

wherein $R_4,R_5$ represent independently hydrogen atom, lower alkyl, carbamoyl, lower alkanoyl, lower alkoxycarbonyl, amidino optionally substituted by lower alkyl and Z is as above defined;

(d)

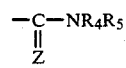

wherein $R_3$ is as defined above and $R_6$ represents hydrogen atom, lower alkyl, carbamoyl, lower alkanoyl, hydroxy, lower alkoxy or aryloxy group;

(e) cyano group
(f) —CH$_2$—X, wherein X represents
  (i) NO$_2$ as such or as its nitronates of formula

wherein $R_7$ is an alkaline metal cation, a hydrogen atom, a lower alkyl, aryl, alkenyl or akynyl of 2–6 carbon atoms, cycloalkyl of 4–6 carbon atoms, heteroaryl, lower alkanoyl or carbamoyl group;
  (ii) —NR$_4$R$_5$ wherein R$_4$,R$_5$ are as above defined;
  (iii)

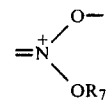

wherein $R_3$, Z are as above defined;
  (iv)

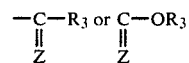

wherein Z, R$_4$ and R$_5$ are as above defined;
  (v) —S(O)$_n$R$_3$ wherein R$_3$ is as defined above and n=0, 1, 2;
  (vi) cyano group or
  (vii) heteroarylthio group optionally saturated,
  (viii) —OR$_8$, wherein R$_8$ is lower alkyl, carbamoyl, alkanoyl, C$_5$–C$_7$ cycloalkylcarbonyl or arylcarbonyl group.

Compounds of formula I wherein the O-protecting and N-protecting groups have been removed are useful as antibiotics, being active against both Gram-positive and Gram negative strains.

The lower alkyl groups referred to above for R, $R_1,R_3,R_4$, $R_5$, $R_6$, $R_7$ and $R_8$ contain 1 to 6 carbon atoms and are exemplified by methyl, ethyl, propyl, butyl, pentyl, hexyl and the corresponding branched chain isomers thereof.

The term "aryl" as used herein for $R_1$, $R_2$, $R_3$, $R_6$, $R_7$ and $R_8$ refers to phenyl, optionally substituted by lower alkyl, lower alkoxy and halogen groups, e.g. p-tolyl, o-tolyl, m-tolyl, p-chlorophenyl, o-methoxyphenyl, etc.

Halogen atoms refer to a fluorine, chlorine, bromine or iodine substituents.

The term "heteroaryl" as used herein for $R_3$, $R_7$ and X (vii) refers to aryl groups having 1 to 4 heteroatoms in the ring such as pyridyl, furanyl, thienyl, thiazolyl, imidazolyl, tetrazolyl or the like. The heteroaryl group may be optionally substituted by 1 to 3 lower alkyl substituents, e.g. 2-methylpyridyl, 3-methylthienyl, 1-methyltetrazolyl, etc.

Where there is a possibility of the various position isomers, the term "heteroaryl" is intended to cover all the isomers, e.g. 2-pyridyl, 3-pyridyl and 4-pyridyl.

The term "aralkyl" denotes lower alkyl groups substituted by one or more aryl groups such as benzyl, phenethyl, benzhydryl and the like. The lower alkanoyl groups referred to above for $R_4$, $R_5$, $R_6$ $R_7$ and $R_8$ contain 1 to 6 carbon atoms and are exemplified by formyl, acetyl, propionyl and butyryl.

The term alkaline metal cation denotes lithium, potassium and sodium cations.

Compounds of formula I wherein Y represents a group of formula (b) to (f) as defined above are known as antibacterial agents being described for example in European Published Applications 2210 and 3960, and in the British Patent Specifications Nos. 2043639 and 2042515.

Additionally, penems of formula I wherein Y is a hydroxymethyl group are useful intermediates for the preparation of useful antibiotics, as described for example in our UK Patent Application Nos. 2,111,496 and 2,118,181.

Included within our inventive concept are also new penam compounds of the following formula IV

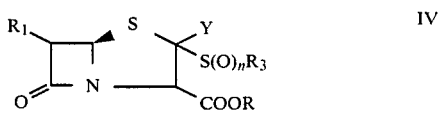

wherein R, $R_1$, $R_3$ and Y are as above defined and n is 0, 1, 2. Compounds (IV) wherein the N- and O-protecting groups have been removed and replaced by hydrogen exhibit antibacterial activity. Thus, another aspect of our invention includes within its scope pharmaceutical compositions comprising an antibacterially effective amount of a penam of formula IV wherein all O- and optionally, all N-protecting groups have been removed together with a compatible, pharmaceutically acceptable carrier or coating. Also included within this invention is the method of eliciting an antibacterial response in a warm-blooded animal having a susceptible bacterial infection which comprises administering to said animal a non-toxic, antibacterially effective amount of a compound of formula IV wherein all O- and optionally N-protecting groups have been removed.

The dosage administered of the penams of this invention is dependent upon the age and weight of the animal species being treated, the mode of administration, and the type and severity of bacterial infection being prevented or reduced. Typically, the dosage administered per day will be in the range of 100–5000 mg. with 500–1000 mg being preferred.

For oral administration, the antibacterial compounds of this invention may be formulated in the form of tablets, capsules, elixirs or the like. Likewie, they may be admixed with animal feed. They may also be applied topically in the form of ointments, both hydrophylic and hydrophobic, in the form of lotions which may be aqueous, non-aqueous or of the emulsion type, or in the form of creams.

The compounds of formula IV wherein all O- and optionally, N-protecting groups have been removed may be utilized in liquid from such as solutions, suspensions and the like for otic and optic use and may also be administered parenterally via intramuscular injection.

A preferred aspect of this invention is directed to compounds of formula (IV) and to a process for preparing compounds of formula I wherein Y represents
 (a)' a hydroxymethyl group
 (b)'

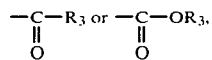

wherein $R_3$ is as defined above,
 (c)'

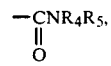

wherein R, R are each independently hydrogen atom, lower alkyl, carbamoyl or lower alkanoyl group;
 (d)'

wherein $R_3$ and $R_6$ are as defined above,
 (e)' a cyano group,
 (f)' —$CH_2$—X', wherein X' represents
  (i) —$NO_2$ as such of as its nitronates of formula

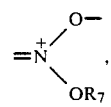

wherein $R_7$ is as above defined;
  (ii)' —$NR_4R_5$ wherein $R_4$, $R_5$ are each independently hydrogen atom, lower alkyl, carbamoyl or lower alkanoyl group;
  (iii)'

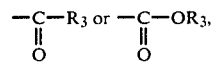

wherein $R_3$ is as above defined;
  (iv)'

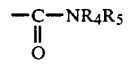

wherein $R_4$ and $R_5$ are as defined above;
  (v)' —S(O)$_n$R$_3$, wherein $R_3$ is as defined above
  (viii)' —$OR_8$ wherein $R_8$ is as defined above.
Particularly preferred compounds prepared according to the process of the present invention are compounds of formula (I) or (IV) wherein $R_1$ is an α-hydroxyethyl group optionally protected and Y represents:
 (a)'' hydroxymethyl group
 (b)''

wherein R₃ is as defined above or (f)″ —CH₂—X″, wherein X″ represents (i)″ —NO₂ as such or as its nitronates of formula

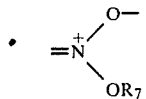

wherein R₇ is as above defined;

(ii)″ —NR₄R₅, wherein R₄, R₅ are as above defined;

(iii)″

wherein R₃ is as defined above, (viii)″ —OR₈, wherein R₈ is above defined.

The compounds of formula (I) and (IV) possess several centers of chirality, and the process of this invention provides compounds having the configuration at C₅ of the absolute stereochemistry R, the 6-substituents may have either α or β orientation, α orientation being preferred.

The most preferred embodiment of this invention is a process directed to the preparation of compounds of the following formula (I″B) having a stereo configuration designated 5R, 6S, 8R and having the following representative spatial configuration:

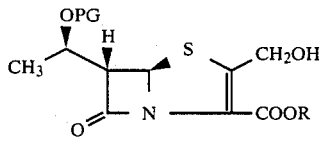

wherein PG is an O-protecting group and R is as defined above. The compounds of formula (I) are prepared by the process of this invention which comprises:
(a) cyclizing an azetidinone (II):

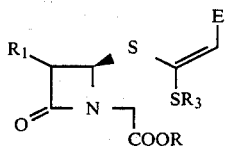

wherein R, R₁ and R₃ are as defined above and E represents an electron withdrawing group selected from heteroarylthio methyl, —NO₂, CN,

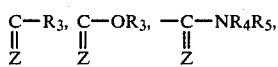

S(O)ₙR₃ groups, wherein R₃, Z and n are as above defined, in tetrahydrofuran, hexane or toluene by treatment with a base at a temperature of from −100° to 0° C., (b) optionally converting if necessary the thereby produced penam of formula (III)

$$\begin{array}{c} R_1 \diagdown \quad S \diagdown \quad CH_2E \\ \quad \diagdown \quad \diagup \quad S(O)_nR_3 \\ O \diagup\!\!\!= \quad N \diagdown \quad COOR \end{array} \quad III$$

wherein E, R, R₁ and R₃ are as defined above, into a penam of formula (IV)

$$\begin{array}{c} R_1 \diagdown \quad S \diagdown \quad Y \\ \quad \diagdown \quad \diagup \quad S(O)_nR_3 \\ O \diagup\!\!\!= \quad N \diagdown \quad COOR \end{array} \quad IV$$

wherein R, R₁, R₃ and Y are as defined above and (c) oxidizing and treating with a tertiary amine or an alkaline metal carbonate the so produced compounds of formula (IV) or (III) in an inert solvent at a temperature of from 0° to 130° C., to give the desired compounds of formula (I), which may optionally be converted into other compounds of formula (I) wherein Y is different.

By "inert solvent" in step (c) is meant any organic or inorganic solvent in which the starting compound and reagent are soluble, and which will not interfere with the process under the reaction conditions thereof, so there are produced a minimum of competing side reactions. Inert solvent which may be used in our process include aromatic hydrocarbons (e.g. benzene, toluene and the like), aliphatic ethers (e.g. diethyl ether, dipropyl ether), cyclic ethers (e.g. dioxane, tetrahydrofuran) and, preferably, halogenated hydrocarbons such as methylene chloride and chloroform.

In the first step (a) of the process, the bases which may be employed are preferably organometallic derivative such as LiN[Si(CH₃)₃]₂, $$LiN(CH\diagup\!\!{}^{CH_3}_{CH_3})_2,$$

n-butyl Li, t-butyl Li, Me Li, phenyl Li and the like.

The oxydation of the step (c) may be carried out by conventional oxydating agents, such as peracids (e.g. metachloroperbenzoic, peracetic acid and the like) or ozone. The tertiary amine is preferably triethylamine, or di-isopropylethyl amine and the alkaline metal carbonate is preferably sodium bicarbonate.

The conversions under step (b) from compounds (III) or (I) to respectively compounds (IV) or (I) wherein Y is different may be performed by well known literature methods.

For example, compounds (IV) or (I) wherein Y represents a group of formula CH₂NR₄R₅ wherein R₄ and R₅ are as defined above may be respectively obtained from compounds (III) or (I) wherein CH₂E or Y represent a nitromethyl group by reduction (e.g. with H₂ in presence of Pd/C) and subsequent optimal alkylation or acylation.

Compounds (IV) or (I) wherein Y represents a formyl group may be respectively obtained from compounds (III) or (I) wherein CH₂E or Y represent a nitromethyl group by basic treatment, optional quenching with an alkylating agent such as CH₃I and subsequent ozonisation. Compounds (I) wherein Y represents a hydroxymethyl group may be obtained from compounds (I) wherein Y represents a formyl group by reduction.

Compounds (I) wherein Y represents a group of formula

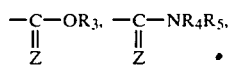

or CN, wherein $R_3$, $R_4$, $R_5$, and Z are as above defined may be obtained from compounds (I) wherein Y represents a formyl group by oxydation and subsequent reactions well known to people skilled in the art.

A preferred embodiment of the process of the present invention is shown via flow diagram as follows:

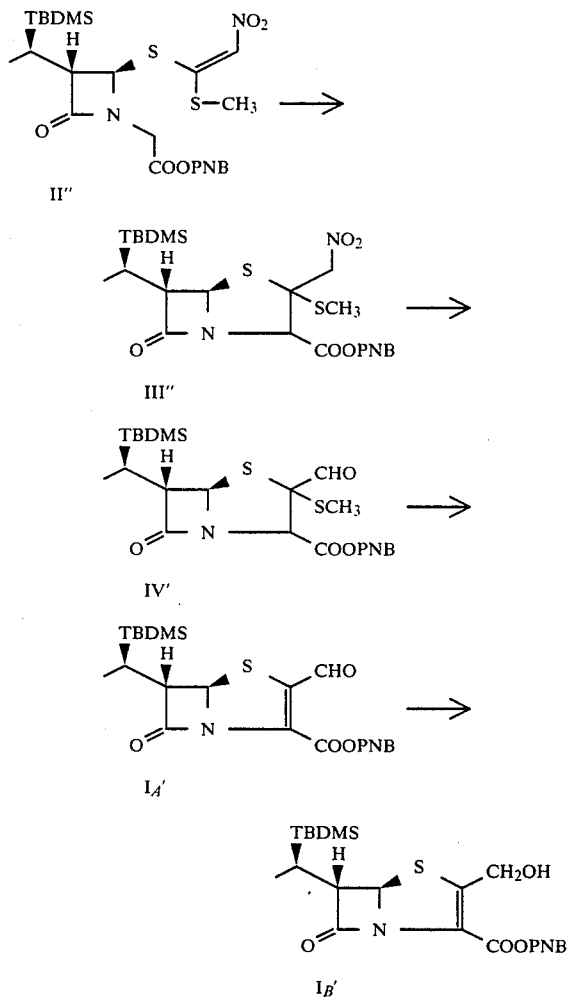

In carrying out this preferred mode of our inventive process, the azetidinzone of formula (II′) [which is a compound of formula (II) wherein $R_1$ is a hydroxyethyl group protected by t-butyldimethylsilyl group, R is p-nitrobenzyl, $R_3$ is a methyl group and E is a nitro group] having the stereoconfiguration 3S, 4R, 5R in a tetrahydrofuran solution is added to a solution containing about 2 molar equivalents of Li-N[Si(CH$_3$)$_3$]$_2$ at $-78°$ C. After 10 minutes reaction time, the obtained compound of formula (III′) is isolated and purified via chromatography on silica gel and crystallization from diisopropyl ether. The compound of formula (IV′) [which is a compound of formula IV wherein Y represents a formyl group] is obtained by treating the compound (III′) with LiN[Si(CH$_3$)$_3$]$_2$ in tetrahydrofuran at $-78°$ C. for 10 minutes, followed by an addition of CH$_3$I and subsequent ozonization. To the so produced penam (IV′) in a chloroform solution at 0° C. there is added about 1.05 molar equivalents of metachloroperbenzoic acid in chloroform. After 10 minutes reaction time, an excess of NaHCO$_3$ is added and the desired penem (I′$_A$) isolated and purified via chromatography on silica gel.

The conversion of compound (I′$_A$) to compound (I′$_B$) is carried out by reaction with L-selectride in tetrahydrofuran at $-78°$ C.

The starting intermediates (II) for the process of the present invention are prepared according the following reaction scheme, wherein L is a leaving group such as an acetoxy or a benzoate group, and R, $R_1$, $R_3$, E and Y are as above defined.

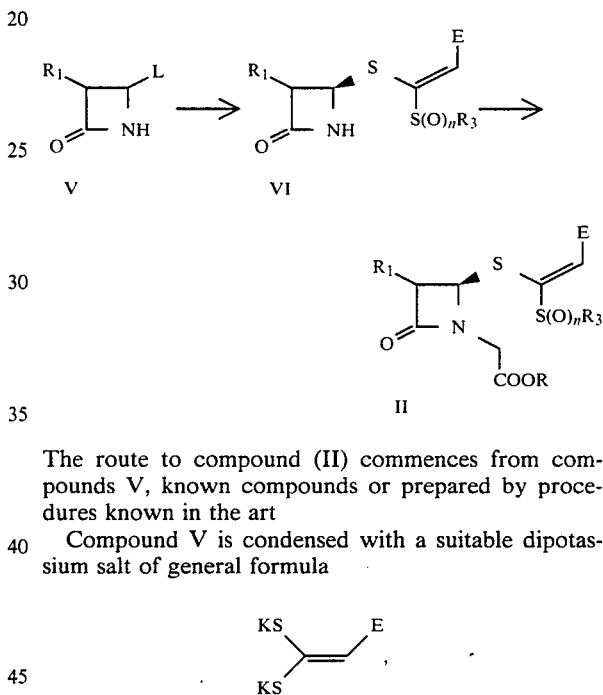

The route to compound (II) commences from compounds V, known compounds or prepared by procedures known in the art Compound V is condensed with a suitable dipotassium salt of general formula already known in literature [e.g. Ber. 52, 542 (1919)] or prepared by analogous procedures, and then alkylated to give compound (VI). The subsequent conversion of compound (VI) in compound II may be performed using well known methods.

The invention is illustrated by the following examples in which the abbreviations PNB for p-nitrobenzyl, and TBDMS for t-butyl-dimetylsilyl are used.

PREPARATION A (3S, 4R)-3[(1R)-tert-butyldimethylsilyloxyethyl]-4-[(1-methylthio-2-nitro)ethylenthio]azetidin-2-one The solution of the dipotassium-2-nitroethylen dithiolate (1.1 g, 4.95 mM) in ETOH (5 mL):water (5 ml) was dropped into a cooled (0° C.) and stirred solution of the 4-acetoxy-3(R)-[(1R)-tert-butyldimethylsilyloxyethyl-]azetidin-2-one (1.44 g, 5 mM) in ethanol (20 mL):water (5 mL).

The mixture was then stirred for a further 10 min. and dimethylsulfate was added at 0° C.

The solution was then stirred over 1 hr at room temperature, cooled again, water (50 mL) was added and the suspension was stirred for 30 min. at 0°. The solid was collected by filtration; washed with small portions of cold EtOH/H$_2$O, collected and dissolved in Et$_2$O. The ethereal solution was dried over anhydrous magnesium sulfate decolorized with charcoal, filtered and evaporated. The solid residue was then crystallized from chloroform/hexanes to give the title compound as a white-yellowish solid, 1.25 g (66%).

m.p. 144°–146° C. (dec) $[\alpha]_D = +215.3$ (c 1.55, CHCl) I.R. (CHCl$_3$ film) cm$^{-1}$: 3300, 1770, 1525 NMR (90 MHz), CDCl$_3$) $\delta$(ppm) 0.08 (3H, s); 0.09 (3H, s); 0.88 (9H, s); 1.25 (3H, d, J=6.5 Hz); 2.62 (3H, s) 3.28 (1H, dd, J=2.6 and 3 Hz); 4.3 (1H,, m); 5.44 (1H, d, J=2.6 Hz); 6.84 (1H, br s); 7.05 (1H, s) Mass: CI: 379 (M+1), 228 (M−150) C$_{14}$H$_{26}$N$_2$O$_4$Si requires: C 44.41; H 6.92; N 7.40; S 16.94 found: C 44.53; H 7.00; N 7.32; S 16.61

PREPARATION B p-Nitrobenzyl {(3S)-[(1R)-tert-butyldimethylsilyloxyethyl]-(4R)-[(1-methylthio-2-nitro)ethylenthio]-2-oxoazetidin-1-yl}-acetate To a solution of (3S, 4R)-3[(1R)-tertbutyldimethylsilyloxyethyl]-4-[(1-methylthio-2-nitro)ethylenthyo]azetidin-2-one (1.51 g, 4 mM) in dry CH$_2$Cl$_2$ (50 mL) at 0° C., were added CaCO$_3$ (2 g), p-nitrobenzyl chlorocarbonyl formate (1.2 g) and diisopropyl ethylamine (0.8 mL) in sequence. The mixture was filtered through celite, washed twice with cold H$_2$O, dried and evaporated in vacuo. The residue was taken up with toluene and purified by a short column of silanized silica gel eluting with toluene −0.5% EtOAc to give 1.7 g of p-nitrobenzyl 2-{(3S)-[(1R)-tert-butyldimethylsilyloxyethyl]-(4R)-[(1-methylthio-2-nitro)ethylenthio]-2-oxo azetidin-1-yl}-2-oxoacetate as a yellow syrup.

IR cm$^{-1}$ (CHCl$_3$) film; 1820, 1760, 1720, 1530. NMR (CDCl$_3$) $\delta$(ppm): 0.1 (6H, s); 0.9 (9H, s); 1.35 (3H, d, J=6.0 Hz); 2.6 (3H, s); 3.5 (1H, dd); 4.4 (1H, m) 5.3 (2H, s); 6.2 (1H, d,, J=3.5 Hz); 7.1 (1H, s); 7.6 (2H, d); 8.25 (2H, d).

The above syrup (1.7 g) was dissolved in CHCl$_3$ (20 mL) and treated with trimethylphosphite (0.77 mL, 6.5 mM) at room temperature under Argon. The solution was then stirred 36 hours at room temperature. The crude product was then purified by colum chromatography yielding 1.55 g of p-nitrobenzyl 2{(3S)-[(1R)-tert-butyldimethylsilyloxyethyl]-(4R)-[(1-methylthio-2-nitro)ethylenthio]-2-oxoazetidin-1-yl}-2-trimethoxy phosphoranylidene acetate.

IR (CHCl$_3$ film) cm$^{-1}$ 1770, 1650, 1530.

The solution of the above phosphoranylidene acetate in THF (50 mL):water (10 mL) and p-toluen sulphonic acid (catalitic amount) was stirred at room temperature for 1 hr. The solution was then poured into 1% aq. NaHCO$_3$ and EtOAc. The organic phase was separated, washed twice with brine, dried and evaporated. The crude residue was purified by column chromatography to give the title compound as a yellow oil (0.82 g).

IR (CHCl$_3$, film), cm$^{-1}$, 1780, 1760 (sh), 1530 NMR $\delta$(ppm) 0.07 (3H, s); 0.09 (3H, s); 0.88 (9H, s); 1.28 (3H, d, J=6.0 Hz); 2.48 (3H, s); 3.25 (1H, dd, J=2.5, 4 Hz); 3.90, 4.09, 4.23, 4.45 (ABq, 2H, J=19 Hz); 4.35 (1H, m); 5.25 (2H, s); 5.78 (1H, d, J=2.5 Hz); 7.0 (1H, s); 7.55 (2H, d, J=8 Hz); 8.25 (2H, d, J=8 Hz). Mass. spectral data: CI: 572 (M+1); 514 (M−C$_4$H$_9$); 421 (M−150).

EXAMPLE 1 p-Nitrobenzyl(5R,6S)-6-[(1R)tert-butyldimethylsilyloxyethyl]-2-methylthio-2-nitromethylpenam-3-carboxylate.

To a solution of hexamethyldisilazane (337 µl,160 mM) in dry TMF (10 mL) at 0° C. under Argon was added a solution of n butyl lithium (1.6M solution in n-hexane) dropwise and with stirring (1 mL, 1.6 mM). The resulting colourless solution was stirred 30 minutes at 0° C. It was then cooled at −78° C. and a solution of p-nitrobenzyl {(3S)-[(1R)-tertbutyldimethylsilyloxyethyl]-(4R)-[(1-methylthio-2-nitro)ethylthio]-2-oxoazetidin-1-yl}acetate (430 mg, 0.75 mM) in TMF (5 mL) was added in 2 minutes.

The resulting dark red solution was stirred at −78° C. over 10 min. and quenched with water containing AcOH. The mixture was let warm to room temperature and then partitioned between EtOAc/H$_2$O. The organic phase was washed twice with salted water, dried, evaporated in vacuo and purified by column chromatography to give the title compound as a waxy solid. It was then cristallized from diisopropyl ether (0.22 g, 51%).

mp 103°–105° C. $[\alpha]_D = +216.9$ (c 0.775 CHCl$_3$) IR (CHCl$_3$, film) cm$^{-1}$1780, 1750, 1560, 1525 NMR (60, 90, 400 MHz, CDCl$_3$) $\delta$(ppm); 0.01 (6H, s); 0.09 (9H, s); 1.26 (3H, d, J=6.3 Hz); 2.33 (3H, s); 3.39 (1H, dd, J=1.8 and 4.5 Hz); 4.15 (1H, s); 4.28 (1H, m); 4.79, 4.82, 5.47, 5.50 (2H, ABq, J=13.4 Hz); 5.20 (1H, d, J=1.8 Hz); 5.29, 5.32, 5.36, 5.39 (2H ABq, J=13 Hz); 7.65 (2H, d, J=9 Hz); 8.25 (2H, d, J=9 Hz). Mass. DCI-HN$_3$: 572 (M+1); 514 (M−C$_4$H$_9$); 372 (M−199) C$_{23}$H$_{33}$N$_3$O$_8$S$_2$Si requires C 48.31; H 5.82; N 7.35; S. 11.22 found C 48.13; H 5.75; N 7.25; S 10,89

EXAMPLE 2 p-Nitrobenzyl(5R,6S)-6[(1R)-tert-butyldimethylsilyloxyethyl]-2-methylthio-2-formylpenam-3-carboxylate.

Method A

To a solution of lithium hexamethyl disilylazide in TMF (5 mL) [prepared as in the preceding example for hexamethyldisilazane (32 µl, 0.15 mM) and n BuLi 1.6M solution in n hexane (95 µl 0.15 mM)]was added the solution of the penam prepared in example 1, at −78° C. in 1 minute under Argon. The dark yellow mixture was stirred 10 min. at −78° C. and CH$_3$I (200 µl) was added. After further 10 min. the mixture was ozonized for 15 min., monitoring the progress by TLC). The excess of ozone was purged with argon and then dimethylsulfide was added (200 ul) together with a few drops of acetic acid (in order to maintain the pH at about 6). The reaction mixture was allowed to warm to 0° C. and then poured immediately in aqueous NaCl solution/ether. The ethereal phase was washed twice with NaCl, dried over MgSO$_4$, evaporated in vacuo in the cold and purified by passing it rapidly through a column of silanized silica gel (eluting with toluene 7/hexane 3) to give the title compound as colourless oil (45 mg).

IR (CHCl$_3$, film): cm$^{-1}$, 1785, 1750, 1725, 1525 NMR (60, 90, 400 MHz, CDCl$_3$) $\delta$(ppm) 0.05 (3H, s); 0.07 (3H, s); 0.86 (9H, s); 1.23 (3H, d, J=6.3 Hz); 2.17 (3H, s); 3.40 (1H, dd, J=1.8 and 4.1 Hz); 4.19 (1H, s); 4.25 (1H, m); 5.21 (1H, d, J=1.8 Hz); 5.23, 5.26, 5.36, 5.39 (2H, ABq, J=13 Hz); 7.56 (2H, d, J=9 Hz); 8.21 (2H, d, J=9 Hz); 9.21 (1H, s). Mass DCI, isobutane: 483 (M-C$_4$H$_9$); 341 (M-199).

Method B

To a solution of lithium hexamethyldisilylazide in TMF (10 mL) [prepared from hexamethyldisilazane (337 μL, 1.60 mM) and n BuLi 1.6 M solution in n hexane (1 mL, 1.6 mM)] was added a solution of p-nitrobenzyl (3S)-[(1R)-tertbutyldimethylsilyloxyethyl]-(4R)-[(-1-methylthio-2-nitro)ethylenthio]-2-oxoazetidin-1-yl}acetate (430 mg, 0.75 mM) in TMF (5 mL) in 2 minutes. The resulting solution was stirred 10' at −78° C. and CH$_3$I (400 μl) was added. After further 10 minutes the mixture was ozonized for 15 minutes. After work-up as described in method A the title compound was obtained (0.11 g) with chemical physical properties identical as in method A.

EXAMPLE 3 p-Nitrobenzyl(5R,6S)-6[(1R)-tert-butyldimethylsilyloxyethyl]-2-formylpenam-3-carboxylate.

To the stirred and cooled (0° C.) solution of p-nitrobenzyl(5R,6S)-6[-(1R)-tert-butyldimethylsilyloxyethyl]-2-methylthio-2-formylpenam-3-carboxylate (54 mg, 0.1 mM) in chloroform (3 mL) was added a solution of metachloroperoxybenzoic acid (21.6 mg, 0.105 mM; 85%) in chloroform (1.5 mL). After 10 minutes the solution was vigorously stirred with a NaHCO$_3$ solution at 0° C. The aqueous phase was separated and the organic phase was stirred vigorously for 30 minutes at room temperature with water.

The aqueous phase was discarded and the organic phase was dried over MgSO$_4$, filtered, washed carefully with chloroform and evaporated repeatedly in vacuo. The crude residue was purified by column chromatography eluting with an EtOAc/hexanes gradient to give the title compound as an amorphous solid (26 mg).

IR (CHCl$_3$, film) cm$^{-1}$: 1790, 1715, 1660, 1520. NMR (CDCl$_3$) δ(ppm) 0.04 (3H, s); 0.08 (3H, s); 0.83 (9H, s); 1.25 (3H, d, J=6.3 Hz); 3.91 (1H, dd, J=2.0 and 3.3 Hz) 4.27 (1H, m); 5.30, 5.33, 5.45, 5.49 (2H, ABq, J=13 Hz); 5.68 (1H, d, J=2.0 Hz); 7.63 (2H, d, J=9 Hz); 8.23 (2H, d, J=9 Hz); 10.42 (1H, s). Mass DCI-isobutane: 435 (M−C$_4$H$_9$); 293 (M−199) UV (CHCl$_3$)λmax (nm): 265, 390.

EXAMPLE 4 p-Nitrobenzyl-(5R,6S)-6-[(1R)-tert-butyldimethylsilyloxyethyl]-2-nitromethylpenem-3-carboxylate.

A solution of metachloroperoxybenzoic acid (85%, 0.105 mM, 21.5 mg) in chloroform (1.5 mL) was added to a stirred and cooled (0° C.) solution of p-Nitrobenzyl-(5R,6S)-6/(1R)tertbutyldimethylsilyloxyethyl/-2-methylthio-2-nitromethylpenam-3-carboxylate (57.1 mg, 0.1 mM) in chloroform (3 mL).

After 10 minutes the solution was vigorously stirred with a NaHCO$_3$ solution at 0° C. The aqueous phase was separated and the organic phase was washed at room temperature with water. The collected organic phase was dried over MgSO$_4$, filtered, and evaporated in vacuo yielding a yellowish oil (20 mg).

IR (CHCl$_3$) cm$^{-1}$: 1795, 1715 UV (CHCl$_3$) max nm: 264, 334 NMR (CDCl$_3$) ppm; 0.01 (3H, s); 0.09 (3H, s); 0.9 (9H, s); 1.32 (3H, d, J=6 Hz), 3.95 (1H, dd, J=1.9 and 3.8 Hz); 4.3 (1H, m); 5.28, 5.35, 5.48 and 5.55 (2H, ABq, J=13.8 Hz); 5.39, 5.47, 6.10 and 6.17 (2H, ABq, J=15 Hz), 5.86 (1H, d, J=1.9 Hz) 7.6 (2H, d, J=9 Hz); 8.23 (2H, d, J=9 Hz). Mass spectral data (FD): 523 (M), 466 (M−C$_4$H$_9$)

EXAMPLE 5 p-Nitrobenzyl(5R,6S)-6-[(1R)-tert-butyldimethylsilyloxyethyl]-2-hydroxymethylpenem-3-carboxylate.

To a solution of p-nitrobenzyl(5R,6S)-6[(1R)-tert-butyldimethylsilyloxyethyl]-2-formylpenem-3-carboxylate (49 mg, 0.1 mM) in THF (10 mL) was added L-selectride 1M solution (100 μl, 0.1 mM) at −78° C. dropwise, under argon and with stirring.

The solution was stirred 5 min. at −78° C. and then quenched with ammonium chloride solution at −78° C. (1 mL). The reaction mixture was warmed at room temperature and then partitioned between EtOAc/H$_2$O. The aqueous phase was extracted twice with EtOAc and the combined organic extracts were washed twice with sodium chloride solution, dried over sodium sulfate, filtered, and evaporated in vacuo. The crude was then purified by column cromatography yielding the title compound as an amorphous solid (31 mg).

UV (CHCl$_3$)λmax: 265, 324. IR (CHCl$_3$, film) cm$^{-1}$: 3400 (br), 1790, 1710, 1525. NMR (400 MHz, CDCl$_3$) δ(ppm); 0.04 (3H, s); 0.08 (3H, s); 0.82 (2H, s); 1.25 (3H, d, J=6.3 Hz); 3.32 (1H, brt, J=7.0 Hz); 3.77 (1H, dd, J=1.7 and 3.8 Hz); 4.26 (1H, m); 4.71 (2H br m); 5.21, 5.25, 5.41, 5.44 (2H, ABq, J=13.7 Hz); 5.64 (1H, d, J=1.7 Hz); 7.62 (2H, d, J=8.7 Hz); 8.23 (2H, d, J=8.7 Hz). Mass spectral data: CI: 495 (M+1); 437 (M−C$_4$H$_9$); 295 (M−199) [α]$_D$ (c1, CHCl$_3$)=+33.5°

EXAMPLE 6 p-Nitrobenzyl(5R,6S)-6-[(1R)-hydroxyethyl]-2-hydroxymethylpenem-3-carboxylate.

To a solution of p-nitrobenzyl(5R,6S)-2-hydroxymethyl-6-[(1R)-tert-butyldimethylsilyloxyethyl]-penem-3-carboxylate (1.2g 2.4 mmol) in THF (50 ml), acetic acid (1.47 ml, 24 mmol) and tetrabutylammonium fluoride (2.27 g, 7.2 mmol) were added.

The resulting mixture was stirred at room temperature for 16 hours. The solution was then evaporated in vacuo and the residue was chromatographed on silica gel eluting with ethyl acetate/cyclohexane mixtures to give the title product as a light yellow solid (775 mg, 85%).

UV (EtOH)λmax 264 , 322. NMR (Acetone) δppm (60 MHZ) 1.45 (3H, d, J=6.5 Hz); 3.67 (1H, dd, J=1.5, 6.0 Hz); 4.10 (1H, m); 4.72 (2H, s); 5.32 (2H, ABq, J=14 Hz, separation of inner lines 8 Hz); 5.59 (1H, d, J=1.5 Hz); 7.69 (2H, d, J=7 Hz); 8.18 (2H, d, J=7 Hz)

EXAMPLE 7

Sodium(5R,6S)-6-[(1R)-hydroxyethyl]-2-hydroxymethylpenem-3-carboxylate

A solution of p-nitrobenzyl(5R,6S)-6-[(1R)-hydroxyethyl]-2-hydroxymethyl-penem-3-carboxylate (450 mg. 1.2 mmol) in EtOAc (25 ml) containing NaHCO$_3$ (100 mg. 1.2 mmol) was hydrogenated over 5% Pd/C (450 mg) under normal pressure for 1 hour. A further amount of 5% Pd/C (750 mg) was then added and the hydrogenation was continued for 1 hour.

The mixture was then filtered and the organic phase was discarded. The aqueous phase was concentrated in vacuo to give a brownish oil which was purified on a reverse phase column eluting with water. The title product was so obtained as an amorphous solid (210 mg 61.2%).

UV (H$_2$O)$\lambda_{max}$ 259, 306 nm NMR (D$_2$O) δppm (90 MHZ) 1.30 (3H, d, J=7 Hz); 3.88 (1H, dd, J=1 and 6.3 Hz); 4.23 (1H, m); 4.63 (2H, ABq, J=14.5 HZ, separation of inner lines=4 Hz); 5.62 (1H, d, J=1 Hz)

EXAMPLE 8

Sodium(5R,6S)-6-[(1R)-hydroxyethyl]-2-methylthio-2-formyl-penam-3-carboxylate.

Starting from p-nitrobenzyl(5R,6S)-6-[(1R)-tert-butyldimethylsilyloxyethyl]-2-methylthio-2-formylpenam-3-carboxylate, prepared in example 2, and operating as described in examples 5 and 6, the title compound was obtained.

What we claim is:

1. A process for the preparation of a compound of formula I

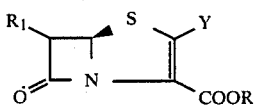

wherein:

R is a hydrogen atom, a lower alkyl group, a 2,2,2-trichloroethyl group, an acetonyl group, an allyl group, a benzyl group, a p-nitrobenzyl group, a p-methoxybenzyl group, a phenyl group, an o-nitrophenyl group, a benzhydryl group, a 1-phenoxyethyl group, or a residue known to be hydrolyzed in vivo and having favorable pharmacokinetic properties, or a group of the formula

wherein:

R$_2$ is C$_1$-C$_5$ alkyl group or an aryl group;

R$_1$ is a hydrogen atom, a lower alkyl group, a lower alkoxy group, a C$_4$-C$_6$ cycloalkyl group, or a hydroxyalkyl group in which the alcoholic function of the hydroxyalkyl group is either free or protected with a protecting group; and Y is:
(a) a hydroxymethyl group,
(b) a —CZ—R$_3$ group or a —CZ—OR$_3$ group, wherein R$_3$ is a hydrogen atom, a lower alkyl group, an arylalkyl group, an aryl group, a heteroalkyl group, a C$_2$-C$_6$ alkenyl group or a C$_2$-C$_6$ alkynyl group, an unsubstituted C$_4$-C$_6$ cycloalkyl group, or a C$_4$-C$_6$ cycloalkyl group substituted by a hydroxy group, a thiol group, an alkylthiol group, a lower alkyl group, a lower alkoxy group, a halogen atom, a cyano group, a carboxy group, a nitro group, an amino group, an amino lower alkyl group, or a halo lower alkyl group, and Z is an oxygen atom or a sulfur atom;
(c) a —CZ—NR$_4$R$_5$ group, wherein R$_4$ and R$_5$ are each independently a hydrogen atom, a lower alkyl group, a carbamoyl group, a lower alkanoyl group, a lower alkoxycarbonyl group, an unsubstituted amidino group, or an amidino group substituted by a lower alkyl group, and Z is as defined in (b) above;
(d) a —C(=NR$_6$)—R$_3$ group, wherein R$_3$ is as defined in (b) above and R$_6$ is a hydrogen atom, a lower alkyl group, a carbamoyl group, a lower alkanoyl group, a hydroxy group, a lower alkoxy group, or an aryloxy group;
(e) a cyano group; or
(f) a —CH$_2$X group, wherein X is (f1) a NO$_2$ group or a nitronate of the formula =N$^+$(O$^-$)(OR$_7$), wherein R$_7$ is an alkaline metal cation, a hydrogen atom, a lower alkyl group, an aryl group, a C$_2$-C$_6$ alkenyl group, a C$_2$-C$_6$ alkynyl group, a C$_4$-C$_6$ cycloalkyl group, a heteroaryl group, a lower alkanoyl group, or an carbamoyl group; (f2) a group —NR$_4$R$_5$ where R$_4$ and R$_5$ are as defined in (c) above; (f3) a —CZ—R$_3$ group or a —CZ—OR$_3$ group where Z and R$_3$ are as defined in (b) above; (f4) a —CZ—NR$_4$R$_5$ group where Z, R$_4$ and R$_5$ are as defined in (b) and (c) above, (f5) a —S(O)$_n$R$_3$ group where R$_3$ is as defined in (b) above and n is 0, 1 or 2; (f6) a cyano group; (f7) an unsaturated heteroarylthio group or a saturated heteroarylthio group; or (f8) a group —OR$_8$, wherein R$_8$ is a lower alkyl group, a carbamoyl group, an alkanoyl group, C$_5$-C$_7$ cycloalkylcarbonyl group or a C$_5$-C$_7$ arylcarbonyl group; said process comprising:

(1) cyclizing an azetidinone of formula (II)

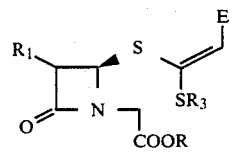

wherein R, R$_1$ and R$_3$ are as defined above, and E is an electron withdrawing group selected from the group consisting of heteroarylthiomethyl groups, NO$_2$, CN, CZ—R$_3$ groups, CZ—OR$_3$ groups, CZ—NR$_4$R$_5$ groups and S(O)$_n$R$_3$ groups, wherein R$_3$, Z and N are as defined above; said cyclization taking place in tetrahydrofuran, hexane or toluene, in the presence of a base, at a temperature of from −100° C. to 0° C., to obtain a penam of formula (III);

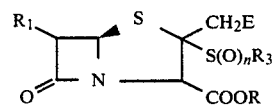

(2) if necessary, converting the penem of formula (III) obtained into a penem of formula (IV)

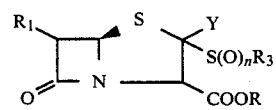

and,
(3) oxidizing the compound of formula (III) or (IV) obtained, and treating the same with a tertiary amine or an alkaline metal carbonate in an inert solvent at a temperature of from 0° C. to 130° C. to obtain a compound of formula (I).

2. The process of claim 1, comprising using a compound wherein R$_1$ is a hydroxy substituted lower alkyl group.

3. The process of claim 1, comprising using a compound wherein R$_1$ is 1-hydroxyethyl.

4. The process of claim 1, comprising using a compound in which $R_1$ is a hydroxyalkyl group in which the alcoholic function is protected with a protecting group, said protecting group being a p-nitrobenzyloxycarbonyl group, a dimethyl-t-butylsilyl group, a diphenyl-t-butylsilyl group, a 2,2,2-trichloroethoxycarbonyl group, a trimethylsilyl group, a benzyl group, a p-bromophenacyl group, a triphenylmethyl group or a pyranyl group.

5. The process of claim 1, comprising converting the compound of formula (I) obtained into a different compound of formula (I) wherein the group Y is different.

6. The process of claim 1, comprising:

(1) reacting the compound of formula ($II_B''$)

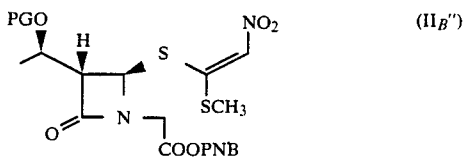

wherein PG is a O-protecting group, with LiN(Si(CH$_3$)$_3$)$_2$ in tetrahydrofuran at a temperature of about $-78°$ C. to obtain a compound of formula (III'')

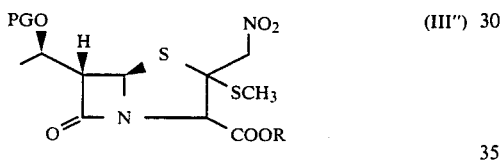

(2) reacting the compound of formula (III'') with LiN(Si(CH$_3$)$_3$)$_2$, CH$_3$I and ozone in tetrahydrofuran at a temperature of about $-78°$ C. to obtain a compound of formula (IV'')

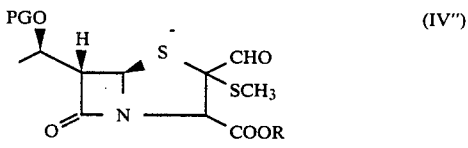

(3) reacting the compound of formula (IV'') with methachloroperbenzoic acid and NaHCO$_3$ in chloroform at a temperature of about 0° C. to obtain a compound of formula ($I_A''$)

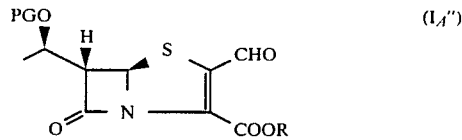

(4) treating the compound of formula (I'') with L-selectride in tetrahydrofuran at a temperature of about $-78°$ C. to obtain a compound of formula ($I_B''$)

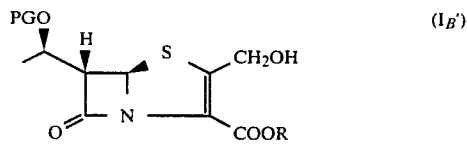

7. The process of claim 6, comprising using as the compound of formula (II'') p-nitrobenzyl ((3s)-[(1R)t-butyldimethylsilyloxyethyl](4R)-[(1-methylthio-2-nitro)ethylthio]-2-oxoazetidin-1-yl) acetate to obtain p-nitrobenzyl-(5R,6S)-6-[(1R)t-butyldimethylsilyloxyethyl]-2-hydroxymethyl-penem-3-carboxylate.

8. The process of claim 1, said process comprising preparing a compound of formula (I)

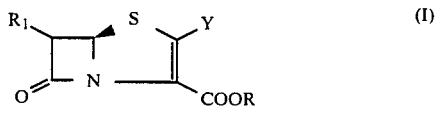

by oxidizing, and treating with a tertiary amine or an alkaline-metal carbonate a compound of formula (IV)

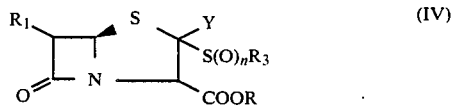

in an inert solvent at a temperature of from 0° C. to 50° C.

9. The process of claim 8, comprising converting the compound of formula (I) obtained into a compound of formula (I) wherein the group Y is different.

* * * * *